United States Patent
Tuffley

(10) Patent No.: US 10,300,028 B2
(45) Date of Patent: May 28, 2019

(54) COMPOSITION AND METHOD FOR ENHANCING WOUND HEALING

(71) Applicant: Mark Tuffley, Brisbane (AU)

(72) Inventor: Mark Tuffley, Brisbane (AU)

(*) Notice: Subject to any disclaimer, the term of this patent is extended or adjusted under 35 U.S.C. 154(b) by 0 days.

(21) Appl. No.: 15/124,321

(22) PCT Filed: Jul. 1, 2014

(86) PCT No.: PCT/AU2014/000689
§ 371 (c)(1),
(2) Date: Sep. 7, 2016

(87) PCT Pub. No.: WO2015/131220
PCT Pub. Date: Sep. 11, 2015

(65) Prior Publication Data
US 2017/0014358 A1  Jan. 19, 2017

(30) Foreign Application Priority Data
Mar. 7, 2014  (AU) ............... 2014900780

(51) Int. Cl.
| | | |
|---|---|---|
| A61K 9/00 | (2006.01) |
| A61K 31/19 | (2006.01) |
| A61K 31/51 | (2006.01) |
| A61K 31/59 | (2006.01) |
| A61K 33/00 | (2006.01) |
| A61K 33/04 | (2006.01) |
| A61K 33/06 | (2006.01) |
| A61K 33/10 | (2006.01) |
| A61K 33/14 | (2006.01) |
| A61K 33/18 | (2006.01) |
| A61K 33/24 | (2006.01) |
| A61K 33/30 | (2006.01) |
| A61K 33/32 | (2006.01) |
| A61K 33/34 | (2006.01) |
| A61K 45/06 | (2006.01) |
| A61K 31/145 | (2006.01) |
| A61K 31/155 | (2006.01) |
| A61K 31/164 | (2006.01) |
| A61K 31/185 | (2006.01) |
| A61K 31/197 | (2006.01) |
| A61K 31/375 | (2006.01) |
| A61K 31/525 | (2006.01) |
| A61K 31/198 | (2006.01) |
| A61K 31/205 | (2006.01) |
| A61K 31/4188 | (2006.01) |
| A61K 31/4415 | (2006.01) |
| A61K 31/455 | (2006.01) |
| A61K 31/519 | (2006.01) |
| A61K 31/714 | (2006.01) |
| A61K 31/555 | (2006.01) |
| A61K 31/7004 | (2006.01) |
| A61K 31/733 | (2006.01) |

(52) U.S. Cl.
CPC .......... *A61K 31/155* (2013.01); *A61K 9/0014* (2013.01); *A61K 31/145* (2013.01); *A61K 31/164* (2013.01); *A61K 31/185* (2013.01); *A61K 31/19* (2013.01); *A61K 31/197* (2013.01); *A61K 31/198* (2013.01); *A61K 31/205* (2013.01); *A61K 31/375* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 31/555* (2013.01); *A61K 31/59* (2013.01); *A61K 31/7004* (2013.01); *A61K 31/714* (2013.01); *A61K 31/733* (2013.01); *A61K 33/00* (2013.01); *A61K 33/04* (2013.01); *A61K 33/06* (2013.01); *A61K 33/10* (2013.01); *A61K 33/14* (2013.01); *A61K 33/18* (2013.01); *A61K 33/24* (2013.01); *A61K 33/30* (2013.01); *A61K 33/32* (2013.01); *A61K 33/34* (2013.01); *A61K 45/06* (2013.01)

(58) Field of Classification Search
None
See application file for complete search history.

(56) References Cited

U.S. PATENT DOCUMENTS

| 4,666,896 A | 5/1987 | Warner, Jr. et al. |
| 4,670,592 A | 6/1987 | Eakin et al. |
| 4,889,844 A * | 12/1989 | Silvetti, Sr. ........ A61K 31/7004 424/672 |

(Continued)

FOREIGN PATENT DOCUMENTS

| CA | 1292943 C | 12/1991 |
| EP | 2226073 A1 | 9/2010 |

(Continued)

OTHER PUBLICATIONS

Mackay, D. et al, Nutritional Support for Wound Healing, Alternative medicine Review, vol. 8, No. 4, pp. 359-377 (2003).
Surjushe A. et al., Aloe Vera: A Short Review, Indian J. Dermatol. 53(4) pp. 163-166 (2008).
Dekker, M., Modern Pharmaceutics, Drugs and Pharmaceutical Sciences, 72: 547-574 (1996).
International Search Report dated Aug. 7, 2014 for Application No. PCT/AU2014/000689, which was filed on Jul. 1, 2014 and published as WO/2015/131220 dated Sep. 11, 2015 (Inventor- Mark Tuffley) (5 Pages).

(Continued)

*Primary Examiner* — Melissa L Fisher
(74) *Attorney, Agent, or Firm* — Ballard Spahr LLP

(57) ABSTRACT

The invention relates to a composition for enhancing wound healing and/or for reducing pain and inflammation, comprising a first active ingredient and a second active ingredient, wherein the first active ingredient comprises an antiseptic and the second active ingredient comprises an admixture of at least one vitamin, at least one mineral and at least one amino acid, and to use of the composition for enhancing wound healing.

20 Claims, 4 Drawing Sheets

(56) References Cited

U.S. PATENT DOCUMENTS

| | | | |
|---|---|---|---|
| 5,164,107 A | 11/1992 | Khan et al. | |
| 2003/0191087 A1* | 10/2003 | Rathjens | A61K 8/73 514/54 |
| 2012/0201902 A1* | 8/2012 | Modak | A01N 31/02 424/618 |

FOREIGN PATENT DOCUMENTS

| | | |
|---|---|---|
| WO | WO-02/055060 A2 | 7/2002 |
| WO | WO-03/061610 A1 | 7/2003 |
| WO | WO-2009/151455 A1 | 12/2009 |
| WO | WO-2011/097347 A2 | 8/2011 |
| WO | WO-2015/131220 A1 | 9/2015 |

OTHER PUBLICATIONS

Written Opinion dated Aug. 7, 2014 for Application No. PCT/AU2014/000689, which was filed on Jul. 1, 2014 and published as WO/2015/131220 dated Sep. 11, 2015 (Inventor- Mark Tuffley) (6 Pages).

International Preliminary Report on Patentability dated Jun. 21, 2016 for Application No. PCT/AU2014/000689, which was filed on Jul. 1, 2014 and published as WO/2015/131220 dated Sep. 11, 2015 (Inventor- Mark Tuffley) (20 Pages).

European Search Report and Opinion dated Jan. 2, 2017 by the European Patent Office for EP Application No. 14884697.5, which was filed on Jul. 1, 2014 and published as EP 3113843 dated Jan. 11, 2017 (Applicant- Mark Tuffley) (8 pages).

Thiruppathi, S. et al., Antimicrobial Activity of *Aloe vera* (L.) Burm. f. Against Pathogenic Microorganisms. J Biosci Res. 1(4):251-8 (2010).

Written Opinion completed on Jun. 2, 2017 by the Intellectual Property Office of Singapore for Application No. 11201607440Y, which was filed on Jul. 1, 2014 and published on Oct. 28, 2016 (Applicant- Mark Tuffley) (6 pages).

\* cited by examiner

A

B

C

D

COMPOSITION AND METHOD FOR ENHANCING WOUND HEALING

CROSS-REFERENCE TO RELATED APPLICATIONS

This application is a U.S. National Phase Application of International Application No. PCT/AU2014/000689, filed Jul. 1, 2014, which claims priority to Australian Patent Application No. 2014900780, filed Mar. 7, 2014. The contents of these earlier filed applications are hereby incorporated by reference herein in their entirety.

TECHNICAL FIELD

The present invention relates to a composition for enhancing tissue healing and/or reducing pain and inflammation.

BACKGROUND

Wounds created by surgery require understanding, careful management and surgical technique to avoid infection thus enhancing the healing response. This is particularly so of wounds created in the mucosal surfaces, for example the mouth where sterility and effective wound dressing is problematic. Treatment of the skin with an antiseptic prior to surgery is effective in reducing the bacterial load to below critical colonisation levels. Accordingly, infection in surgery can be reduced, for example, by painting the skin with iodine or chlorhexidine solutions prior to making an incision. This is more difficult in the mucosa, particularly the mouth, where secretion of biological fluids such as saliva constantly washes and potentially contaminates a treated area. Therefore, the mouth is prepared for surgery by physically cleaning an area to remove biofilm, with the application of topical antiseptics, generally as a mouthwash.

Antiseptics are used to reduce the levels of microorganisms on the skin and mucous membranes. The skin and the mucous membranes of the mouth, nose, gastro-intestinal and genito-urinary tracts are home to a large number of relatively harmless, commensal microorganisms. However, when the skin or mucous membranes are damaged or breached in surgery, antiseptics can be used to disinfect the area and reduce the chance of infection. The antiseptics include alcohols, quaternary ammonium compounds, iodine and phenol compounds. The alcohols used are commonly ethanol, 1-propanol, 2-propanol or mixtures of these alcohols. Quaternary ammonium compounds include the compounds benzalkonium chloride, cetyl trimethyl ammonium bromide, cetylpyridinium chloride and benzethonium chloride.

A further class of antiseptics is the bis-biguanide compounds. The bis-biguanide compounds are well known compounds whose activity is as a chemical antiseptic. They are known to be effective on both Gram-positive and Gram-negative bacteria. The compound most commonly used is chlorhexidine. It is often formulated in oral rinses and skin cleansers, and is used in small quantities as a preservative. It may also be used orally in gel form. Chlorhexidine has both bactericidal and bacteriostatic mechanisms of action. The mechanism of action is thought to involve membrane disruption. Examples of bis-biguanide compounds and their use as antiseptics are provided by U.S. Pat. Nos. 4,670,592, 4,666,896 and 5,164,107.

Iodine may be used in an alcoholic solution, called a tincture of iodine. Iodine is also used as a complex with povidone, a water soluble polymer containing triiodide ions. Further, antiseptics include octenidine dihydrochloride, a cationic surfactant, phenol, sodium chloride and sodium bicarbonate.

However, antiseptics of the type traditionally used to sterilise wounds are cytoirritants which induce macrophages. Macrophages are cells produced by the differentiation of monocytes in tissues. Macrophages function in both non-specific defence as well as in helping initiate specific defence mechanisms. Macrophages play a critical role in inflammatory and immunological processes, various phenotypes being involved in both damaging inflammation as well as tissue repair. The divergent effects of macrophages may be explained by their classification into two main interchangable groups. M1 macrophages, or classically activated macrophages, are immune effector cells that are aggressive against microbes and can engulf and digest effective cells. M1 macrophages are activated by lipopolysaccharides and interferon-gamma. Alternatively activated macrophages, designated as M2 macrophages, are a phenotypic grouping involved in wound healing and tissue repair as well as turning off damaging inflammatory, immune system activation by producing anti-inflammatory cytokines such as interleukin-10. M2 macrophages however do not impede immune competence i.e. non immunosuppressive but act via non-inflammatory pro-resolving routes; they also possess powerful pain down-regulation properties, the mediators being in the picogram to nanogram range. Cytokines, such as Maresins [macrophage mediator in resolving inflammation] are part of a group of specialized pro-resolving lipid mediators which are actively biosynthetised during the resolution phase of acute inflammation and are potent agonists, controlling the magnitude and duration of inflammation.

Alternatively activated macrophages are activated by interleukin-4. M1 macrophages produce nitric oxide and reactive oxygen species, making them cytotoxic. Furthermore, they secrete high amounts of pro-inflammatory cytokines, for example IL-12, that promote inflammation. Conversely, M2 macrophages produce anti-inflammatory cytokines such as IL-10, thereby reducing inflammation. Alternatively activated macrophages also produce high levels of fibronectin and matrix-associated proteins, and they promote fibrogenesis from fibroblastoid cells. The induction of arginase in these cells may lead to polyamine and proline biosynthesis, promoting cell growth, collagen formation and tissue repair. A wide range of specialized pro-resolving lipid mediators [SPMs] have been identified i.e. they act to restore of tissue homeostasis with the resolution of aggressive inflammation. This process is highly regulated.

Early in the innate immune response, macrophages produce reactive oxygen species and pro-inflammatory cytokines to drive inflammation. At this stage, the macrophages are classically activated macrophages. During resolution of inflammation, they switch to an alternatively activated phenotype and contribute to debris scavenging, angiogenesis and wound healing. Macrophage differentiation can also be skewed during differentiation in vitro through provision of alternative cytokines (IL-10 or IL-12) per the previous discussion.

As antiseptics of the type traditionally used to sterilise wounds are cytoirritants, there is an inherent tension in treating the area around a wound with an antiseptic; the antiseptic will have cytoirritant effect and therefore tend to induce inflammation. Classically activated macrophages will be present in the surgical wound in view of the disruption of the tissue. Thus, the inflammation effect is enhanced and wound healing is slowed when antiseptic is applied. It would be desirable to provide a composition which is effective in preventing sepsis but which does not increase damaging inflammation with enhancement of epidermal and mucosal healing, reduction of pain with resolution of inflammation

SUMMARY

A first aspect provides a composition for enhancing wound healing and/or for reducing pain and inflammation in a subject, the composition comprising a first active ingredient and a second active ingredient, wherein the first active ingredient comprises an antiseptic and the second active ingredient comprises an admixture of at least one vitamin, at least one mineral and at least one amino acid.

A second aspect provides a method of enhancing wound healing and/or reducing pain and inflammation in a subject, said method comprising the steps of administering to the subject a therapeutically effective amount of a composition comprising a first active ingredient and a second active ingredient, wherein the first active ingredient comprises an antiseptic and the second active ingredient comprises an admixture of at least one vitamin, at least one mineral and at least one amino acid.

An alternative second aspect provides: use of a composition comprising a first active ingredient and a second active ingredient, wherein the first active ingredient comprises an antiseptic and the second active ingredient comprises an admixture of at least one vitamin, at least one mineral and at least one amino acid, in the manufacture of a medicament for enhancing wound healing and/or reducing pain and inflammation in a subject; or a composition comprising a first active ingredient and a second active ingredient, wherein the first active ingredient comprises an antiseptic and the second active ingredient comprises an admixture of at least one vitamin, at least one mineral and at least one amino acid for use in enhancing wound healing and/or reducing pain and inflammation in a subject.

A third aspect provides a method of enhancing wound healing in a subject, said method comprising the steps of administering to the subject a therapeutically effective amount of a composition comprising a first active ingredient and a second active ingredient, wherein the first active ingredient comprises an antiseptic and the second active ingredient comprises an admixture of at least one vitamin, at least one mineral and at least one amino acid.

An alternative third aspect provides: use of a composition comprising a first active ingredient and a second active ingredient, wherein the first active ingredient comprises an antiseptic and the second active ingredient comprises an admixture of at least one vitamin, at least one mineral and at least one amino acid, in the manufacture of a medicament for enhancing wound healing in a subject; or a composition comprising a first active ingredient and a second active ingredient, wherein the first active ingredient comprises an antiseptic and the second active ingredient comprises an admixture of at least one vitamin, at least one mineral and at least one amino acid for use in enhancing wound healing in a subject.

A fourth aspect provides a method for reducing pain and inflammation in a subject, said method comprising the steps of administering to the subject a therapeutically effective amount of a composition comprising a first active ingredient and a second active ingredient, wherein the first active ingredient comprises an antiseptic and the second active ingredient comprises an admixture of at least one vitamin, at least one mineral and at least one amino acid.

An alternative fourth aspect provides: use of a composition comprising a first active ingredient and a second active ingredient, wherein the first active ingredient comprises an antiseptic and the second active ingredient comprises an admixture of at least one vitamin, at least one mineral and at least one amino acid, in the manufacture of a medicament for reducing pain and inflammation in a subject; or a composition comprising a first active ingredient and a second active ingredient, wherein the first active ingredient comprises an antiseptic and the second active ingredient comprises an admixture of at least one vitamin, at least one mineral and at least one amino acid for use in reducing pain and inflammation in a subject.

A fifth aspect provides a method of treating a wound in a subject, comprising applying to the wound a therapeutically effective amount of a composition comprising a first active ingredient and a second active ingredient, wherein the first active ingredient comprises an antiseptic and the second active ingredient comprises an admixture of at least one vitamin, at least one mineral and at least one amino acid.

An alternative fifth aspect provides use of a composition comprising a first active ingredient and a second active ingredient, wherein the first active ingredient comprises an antiseptic and a second active ingredient comprises an admixture of at least one vitamin, at least one mineral and at least one amino acid, in the manufacture of a medicament for treating a wound in a subject; or a composition comprising a first active ingredient and a second active ingredient, wherein the first active ingredient comprises an antiseptic, and the second active ingredient comprises an admixture of at least one vitamin, at least one mineral and at least one amino acid, for use in treating a wound in a subject.

A sixth aspect provides a kit comprising a composition comprising a first active ingredient and a second active ingredient, wherein the first active ingredient comprises an antiseptic and a second active ingredient comprises an admixture of at least one vitamin, at least one mineral and at least one amino acid.

A seventh aspect provide a kit comprising a first active ingredient comprising an antiseptic and a second active ingredient comprising an admixture of at least one vitamin, at least one mineral and at least one amino acid.

An eighth aspect provides a method of producing a composition for enhancing wound healing and/or for reducing pain and inflammation in a subject, comprising combining a first active ingredient with a second active ingredient, wherein the first active ingredient comprises an antiseptic, and the second active ingredient comprises an admixture of at least one vitamin, at least one mineral and at least one amino acid. In one embodiment, enhancing wound healing comprises enhancing epidermal and mucosal healing.

DETAILED DESCRIPTION

Figure 1:
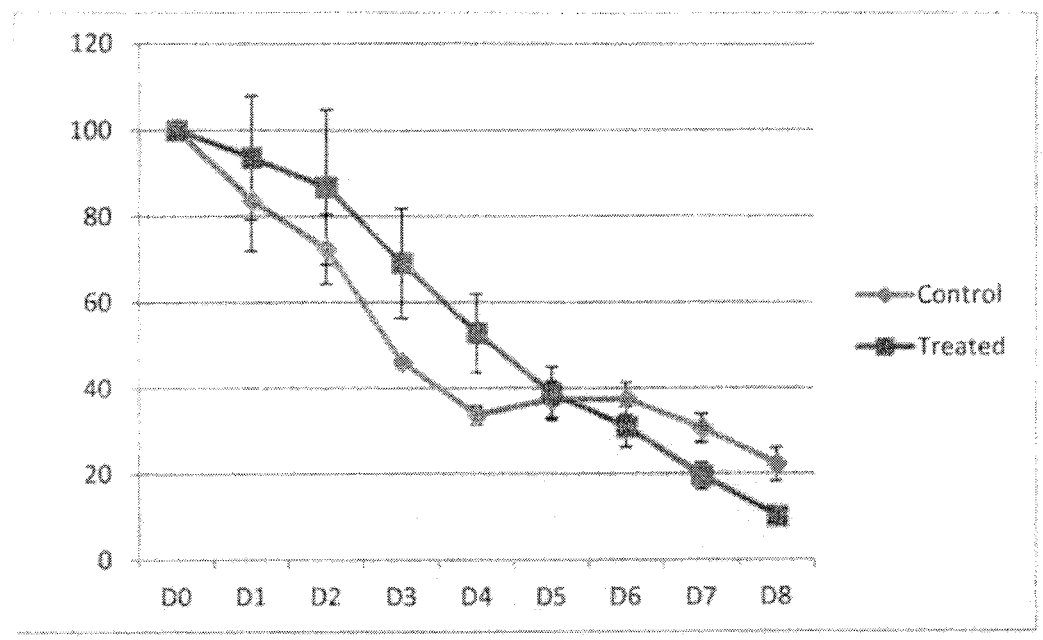
FIG. 1 is a graph showing percentage of wound closure for a control group of mice and a group of mice treated (from day 2) in accordance with the present invention versus time over a period of 8 days (D1 being day 1, D2 being day 2, and so on)

It is to be understood that this invention is not limited to particularly exemplified methods and may, of course, vary. It is also to be understood that the terminology used herein is for the purpose of describing particular embodiments of the invention only, and is not intended to be limiting which will be limited only by the appended claims.

It is to be clearly understood that although prior art publication(s) may be referred to herein, this reference does not constitute an admission that any of these documents forms part of the common general knowledge in the art in Australia or in any other country.

All publications, patents and patent applications cited herein, whether supra or infra, are hereby incorporated by reference in their entirety. However, publications mentioned herein are cited for the purpose of describing and disclosing the protocols and reagents which are reported in the publications and which might be used in connection with the invention. Nothing herein is to be construed as an admission that the invention is not entitled to antedate such disclosure by virtue of prior invention.

Furthermore, the practice of the present invention employs, unless otherwise indicated, conventional chemistry and pharmacology within the skill of the art. Such techniques are well known to the skilled worker, and are explained fully in the literature. See, for example, The Merck Index, 12th Edition (1996), Therapeutic Category and Biological Activity Index; Remington's Pharmaceutical Sciences, 17th Edition (Mack Publishing Company); and Guyton and Hall "Textbook of Medical Physiology" $9^{th}$ Edition (W.B. Saunders Company).

In the claims which follow and in the preceding description of the invention, except where the context requires otherwise due to express language or necessary implication, the word "comprise" or variations such as "comprises" or "comprising" is used in an inclusive sense, ie. to specify the presence of the stated features but not to preclude the presence or addition of further features in various embodiments of the invention. It must be noted that as used herein and in the appended claims, the singular forms "a", "an", and "the" include plural reference unless the context clearly dictates otherwise. Thus, for example, a reference to "a mineral" includes a plurality of such minerals, and a reference to "an amino acid" is a reference to one or more amino acids, and so forth. Unless defined otherwise, all technical and scientific terms used herein have the same meanings as commonly understood by one of ordinary skill in the art to which this invention belongs.

In an embodiment, the composition may be used in the treatment of wounds. The wound may be any type of wound in any part of the body. As used herein, a "wound" is a region of damaged tissue. The damaged tissue may be due to trauma [e.g. mechanical, such as wounds from surgical procedures (including incisions, tooth extractions, or other surgical procedures), wounds from accidents], infection, and/or inflammation. Examples of wounds include: wounds resulting from an incision such as cutting instrument (e.g. incision in surgery), lacerations (typically caused by blunt or broken instrument), puncture wounds, abrasions, burn wounds resulting from exposure to heat, electricity, radiation (for example, sunburn and laser surgery); wounds resulting from surgical procedures such as tooth extraction; caustic chemicals; skin wounds due to aging or the environment, including for example split, dry skin; ulcers (lesion on the surface of the skin or a mucous surface); wounds in subjects suffering from Diabetes Mellitus, including foot injuries due to numbness caused by nerve damage (diabetic neuropathy) and low blood flow to the legs and feet, foot ulcers, decubitus wounds, decubitus (bedsores).

In one embodiment, the wound is a mucosal or epidermal lesion. As used herein, epidermal lesions are lesions of the skin. As used herein, mucosal lesions are lesions of a mucous membrane. The mucous membrane may be any mucous membrane of the body, including oral mucosa, olfactory mucosa, nasal mucosa, genito-urinary tract mucosa. In one embodiment, the mucosal membrane is the oral mucosa. Epidermal lesions may include: wounds, such as those resulting from surgical procedures, accidents, etc; lesion resulting from infection; inflammation; and/or ulceration of the skin. Mucosal lesions include: ulceration, including aphthous ulceration (e.g. canker sores, recurrent apthous stomatitis, recurrent ulcerative stomatitis); periodontal disease; mucositis or eruptions of lichen planus, pemphigus vulgaris, microbial infections; wounds caused by trauma to the mucosal membrane [e.g. wounds from surgical procedures (including incisions, tooth extractions, or other surgical procedures), wounds from accidents]. Wounds may be non-healing areas of the mouth, such as non-healing areas of exposed jaw in, for example, medically compromised patients.

The inventor has found that the composition described herein, when applied to wounds, results in rapid healing of tissue in the wound. The inventor has found that the composition described herein enhances healing of underlying tissue including submucosal and dermal tissue. Without wishing to be bound by theory, the inventor believes that it is the enhancement, by the composition described herein, of healing of the underlying tissue which aids in the enhanced healing of wounds, and in some embodiments, may result in less scarring.

It will be appreciated that the term "enhancing", "enhance", and "enhancement" refers to an increase in the rate of healing of the subject as demonstrated by more complete healing at predetermined time from the commencement of treatment of the wound. Similarly, the terms "treating," "treatment" and the like are used herein to mean affecting the tissue or cells of an individual to increase the rate of healing as demonstrated by more complete healing at predetermined time from the commencement of treatment of the wound.

It will be appreciated that the terms "reducing", "reduce", and "reduction" refer to a decrease in the amount of pain felt by a patient as judged by the patient on a scale of 1 to 10 over the course of treatment and a decrease in inflammation refers to a lessening in the visible signs of inflammation at a predetermined time from the commencement of treatment.

As used herein, "antiseptics" are chemical agents that slow or stop the growth of microorganisms on external surfaces of the body and help prevent infections. It is observed that epidermal and mucosal healing is enhanced and that there is a reduction in pain and inflammation in patients treated with compositions of the invention. While not wishing to be bound by theory, it is believed that at least the cytoirritant effect of the antiseptic in a composition is ameliorated or overcome by coformulation with at least one vitamin, at least one mineral and at least one amino acid. Further, while not wishing to be bound by theory, it is believed that formulations in accordance with the invention induce or allow more rapid transition among macrophages from the classically activated state to the alternatively activated phase in which wound healing is enhanced and pain and inflammation are reduced.

The composition comprises a first active ingredient comprising an antiseptic.

In one embodiment, the antiseptic is a bis-biguanide compound. Bis-biguanide compounds are a class of chemically related compounds known for their bactericidal properties. Generally, bis-biguanide compounds are of the generic formula: $R_1R_2N.C(:NR_6)NH.C(:NH)NH.(CH_2)_n NH.C(:NH)NH.C(:NR_7)NR_3R_4$ where $R_1$, $R_2$, $R_3$ and $R_4$ represent organic groups, and may be the same or different, particularly alkyl, substituted alkyl, aryl or substituted aryl, n is integer, typically greater than 3 and often 5 or 6, and $R_6$ and $R_7$ are hydrogen or an organic group, typically alkyl or substituted alkyl. Examples of bis-biguanide compounds include alexidine and chlorhexidine. Other examples of bis-biguanide compounds are described in U.S. Pat. No. 4,670,592. In one embodiment, the first active ingredient comprises chlorhexidine. Chlorhexidine, also known as bis (5-(p-chlorophenyl)biguanidinio)hexane, hexamethylenebis (5-(4-chlorophenyl)biguanide) and N,N'-bis(4-chlorophenyl)-3,12-diimino-tetraazatetradecanediimidamide, is represented by the formula $C_{22}H_{30}Cl_2N_{10}$ and the structure

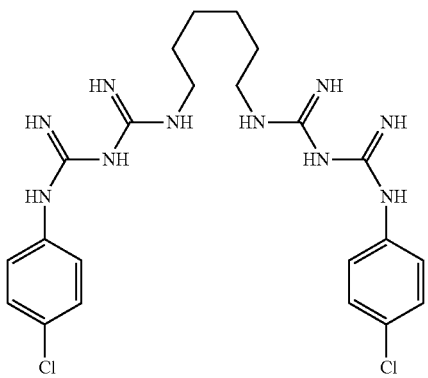 [SMILES: N=C(NCCCCCCNC(=N)NC(=N)Nc1ccc(Cl)cc1)NC(=N)Nc1ccc(Cl)cc1]

Chlorhexidine is generally supplied in the form of chlorhexidine digluconate, due to its good solubility and easy handling; however, the composition of the present invention may utilize chlorhexidine in any form known in the art, for example, chlorhexidine salt, chlorhexidine-digluconate, chlorhexidine-gluconate, chlorhexidine-diacetate or chlorhexidine-dihydrochloride. Other examples of chlorhexidine compounds are described in U.S. Pat. Nos. 4,666,896 and 5,164,107. In one embodiment, the chlorhexidine is in the form of chlorhexidine-digluconate. In another embodiment, the chlorhexidine is in the form of a gel comprising 0.5% chlorhexidine-digluconate.

In another embodiment the bis-biguanide compound is alexidine.

In another embodiment, the antiseptic is a quaternary ammonium compound.

In one embodiment, the quaternary ammonium compound is selected from the group consisting of benzalkonium chloride cetrimide, methylbenzethonium chloride, benzethonium chloride, cetalkonium chloride, cetylpyridinium chloride, dofanium chloride and domiphen bromide.

In one embodiment, the antisepatic is iodine. Iodine antiseptic may be in the form of, for example: a tincture in an alcohol such as ethanol, or a mixture of ethanol and water; Lugol's iodine such as iodine or iodide in water; or as Povidone iodine. Accordingly, in an embodiment, iodine is present as a complex with a water soluble polymer, povidone. In an alternative embodiment, iodine is applied to the skin as a tincture.

In another embodiment, the antiseptic is an antibacterial dye. In an embodiment, the antibacterial dye is selected from the group consisting of proflavine hemisulfate, triphenylmethane, brilliant green, crystal violet and gentian violet.

In another embodiment, the antiseptic is a halogenated phenol derivative. In an embodiment, the halogenated phenol derivative is selected from the group consisting of chlorocresol, chloroxylenol, chlorophene, hexachlorophene and triclosan.

In another embodiment, the antiseptic is a quinolone derivative. In an embodiment, the quinolone derivative is selected from the group consisting of hydroxyquinoline sulfate, potassium hydroxyquinoline sulfate, chlorquinaldol, dequalinium chloride and di-iodohydroxyquinoline.

In addition to an antiseptic, the composition comprises a second active ingredient comprising an admixture of at least one vitamin, at least one mineral and at least one amino acid.

The term "vitamin" as used herein refers to an organic substance other than proteins, carbohydrates, and fats that is an essential constituent of the food of the animal. For the most part vitamins are substances that play an essential part in animal metabolic processes but which the animal cannot synthesise. However, certain animals can synthesise certain compounds of this group and all animals needing vitamin D can synthesise it in the presence of UV light. The vitamins are a well characterised group, and are generally named using letters of the alphabet. Specific examples are vitamin A, B group vitamins including vitamin B1 (thiamine, thiamine hydrochloride), vitamin B2 (riboflavin), vitamin B3 (niacin, niacinamide), vitamin B5 (pantothenic acid, calcium pantothenate), vitamin B6 (pyridoxine, pyridoxine hydrochloride), vitamin B12 (cyanocobalamin), folic acid (folate), biotin, vitamin C (ascorbic acid), vitamin D, vitamin E and vitamin K. In an embodiment, the vitamins in said admixture of vitamins and minerals comprises thiamine, riboflavin, niacin, vitamin C, vitamin D, vitamin E, vitamin B6, vitamin B12, pantothenate, biotin and folate.

As used herein the term "minerals" refers to trace elements required for normal metabolism. Minerals required for this purpose include sodium, magnesium, potassium, calcium, zinc, manganese, copper, selenium, and chromium. Examples of minerals that may be useful in the admixture of vitamins and minerals include sodium chloride, magnesium gluconate, potassium iodide, potassium chloride, calcium, zinc sulphate monohydrate, manganese sulphate, sodium molybdate, copper sulphate, sodium selenite, chromium III chloride and chromium picolinate. The composition may comprise salts or electrolytes additional to or in place of the minerals present in said admixture of vitamins and minerals. In particular, the electrolytes may include cations selected from calcium, magnesium, potassium and sodium and anions selected from chloride, phosphate, picolinate, sulfate and lactate.

As used herein the term "amino acids" refers to the L- or D-isomers of the natual amino acids. Examples of amino acids that may be used include L or D isomers of isoleucine, alanine, leucine, asparagine, lysine, aspartic acid, methionine, cysteine, phenylalanine, glutamic acid, threonine, glutamine, tryptophan, glycine, val me, proline, selenocysteine, serine, tyrosine, arginine, histidine, and ornithine.

In one embodiment, the mineral is selected from the group consisting of sodium, magnesium, potassium, calcium, zinc, manganese, molybdenum, copper, selenium and chromium or salt thereof or combination thereof, the vitamin is selected from the group consisting of thiamine, riboflavin, niacin, vitamin C, vitamin D, vitamin E, vitamin B, vitamin B6 (pyridoxine), vitamin B12, pantothenic acid, biotin and folate or combination thereof and the amino acid is selected from the group consisting of glutamine, lysine, arginine and glycine or combination thereof. In another embodiment, the composition further comprises is at least 10% sodium chloride or calcium carbonate.

In an embodiment said admixture further comprises a component selected from the group consisting of dietary fibre including soluble fibre, carbohydrates, bioflavonoids, fatty acids including essential fatty acids and flavouring agents. The carbohydrate component may be a simple sugar. The sugar is preferably glucose, although may additionally or alternatively be dextrose, fructose, galactose, sucrose (in any of its forms including white sugar, raw sugar and brown sugar), or other sweeteners. The admixture of vitamins and minerals may also contain other components such as carnitine, glucosamine, taurine, sodium citrate, flaxseed oil and/or other Omega 3 rich oils and micellular casein.

The composition will be administered as a therapeutically effective amount to a subject for enhancing wound healing. Proportionately smaller or larger doses can be appropriate for subjects having lesser or greater body weight. Such a dose can be administered as needed, but typically administration 1 to 10 times per day, in most cases 1 or 2 times a day, provides adequate continuing relief of pain.

A "therapeutically effective amount" as used herein is intended to mean the amount administered to a subject which when tested in a standardized test involving observation of the rate of healing. In one such test as described herein below, a clinician scores wound closure over a period of days by pixel analysis of an image of the wound and averaging the score for a cohort. A score as a percentage of initial wound size is provided in such a test, as exemplified herein, and graphed to follow the progression of wound healing. A enhancement is achieved, and the wound is more completely healed by day 7 [168 hours]. The skilled artisan will appreciate, however, that other approaches can be used to assess the severity of pain and relief from such pain.

The terms "subject" or "individual" are used interchangeably herein to refer to any member of the class mammalia, including, without limitation, humans and other mammals such as primates, including non-human primates such as chimpanzees and other apes and monkey species; farm animals such as cattle, sheep, pigs, goats and horses; domestic mammals such as dogs and cats; laboratory animals including rodents such as mice, rats and guinea pigs. The terms do not denote a particular age. Thus, both adult and newborn individuals are intended to be covered.

Thus provided is the treatment for administration to mammals such as humans, as well as those mammals of economical importance and/or social importance to humans, for instance, carnivores other than humans (such as cats and dogs), swine (pigs, hogs, and wild boars), ruminants (such as cattle, oxen, sheep, giraffes, deer, goats, bison, and camels), and horses.

Therefore, one aspect of the present invention involves a method of enhancing wound healing and/or for reducing pain and inflammation in which a composition comprising the composition of the present invention is administered to a subject, in a formulation which provides more complete healing at predetermined time from the commencement of treatment of the wound. The invention is not limited to use of any particular type of formulation. Examples of suitable formulation types are described below.

The terms "administration", "administering", and "administered" are used herein interchangeably. Subject to the limitations inherent in treatment of wounds, such as epidermal and mucosal lesions, including trauma or incisions, the composition of the present invention may be administered topically in dosage unit formulations containing conventional non-toxic pharmaceutically acceptable carriers, adjuvants, and vehicles. In some embodiments the composition of the present invention is administered together with a pharmaceutically acceptable carrier or diluent compatible with the composition. In preparing such composition, any conventional pharmaceutically acceptable carrier can be utilised.

The carrier material can be an organic or inorganic inert carrier material suitable for oral administration. Suitable carriers include water, gelatin, gum arabic, lactose, starch, magnesium stearate, talc, vegetable oils, polyalkylene-glycols, glycerol and the like. Furthermore, the pharmaceutically active preparations may contain other pharmaceutically active agents. Additionally, additives such as flavouring agents, preservatives, stabilisers, emulsifying agents, buffers and the like may be added in accordance with accepted practices of pharmaceutical compounding.

For topical administration to the skin or mucous membrane the aforementioned composition of the present invention may be prepared as an ointment, tincture, cream, gel, solution including a mouth wash, lotion, spray, aerosol, dry powder for inhalation, suspension, and the like. In fact, any conventional methods of preparing topical compositions can be utilised in this invention. Among the preferred methods of applying the composition of the present invention is in the form of a mouthwash, ointment, gel, cream, lotion, spray, aerosol, or dry powder, particularly a mouthwash or a gel. A pharmaceutical preparation for topical administration to the skin can be prepared by mixing the composition of the present invention with non-toxic, therapeutically inert, solid or liquid carriers customarily used in such preparation.

In preparing the topical preparations described above, additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilised in these preparations are included N-methyl-α-tocopherolamine, tocopherols, butylated hydroxyanisole, butylated hydroxytoluene, ethoxyquin and the like.

Ointment formulations containing the composition of the present invention may comprise admixtures of a semi-solid petroleum hydrocarbon with a solvent dispersion of the composition. Cream compositions containing the composition of this invention may comprise emulsions formed from a water phase of a humectant, a viscosity stabiliser and water, an oil phase of a fatty acid alcohol, a semi-solid petroleum hydrocarbon and an emulsifying agent and a phase containing the composition dispersed in an aqueous stabiliser-buffer solution. Stabilisers may be added to the topical preparation. Any conventional stabiliser can be utilised in accordance with this invention. In the oil phase, fatty acid alcohol components function as a stabiliser. These fatty acid alcohol components are derived from the reduction of a long-chain saturated fatty acid containing at least 14 carbon atoms.

Formulations for aerosols are described in Drugs and Pharmaceutical Sciences, Marcel Dekker, New York, 72: 547-574 (1996). Furthermore, the composition of the present invention can be delivered by dry powder inhalation. Such formulations and devices are described in Pharmaceutical. Technology, June 1997, pp. 117-125.

The formulation may in any physical form which suitable for administration to a wound, such as an epidermal or mucosal lesion.

In an embodiment, the antiseptic is formulated with pharmaceutically acceptable excipients in the form of a gel. The gel may comprise 0.01% to 10% antiseptic. In an embodiment the gel may comprise 0.05% to 5% antiseptic, preferably 0.1% to 3% antiseptic, more preferably 0.2% to 2% antiseptic, more preferably 0.3% to 1% antiseptic, more preferably 0.4% to 0.8% antiseptic and most preferably 0.5% antiseptic.

In an embodiment, the antiseptic is formulated with pharmaceutically acceptable excipients in the form of a solution capable use as a mouthwash or for topical application. The solution may comprise 0.001% to 5% antiseptic. In an embodiment the gel may comprise 0.01% to 3% antiseptic, preferably 0.03% to 1% antiseptic, more preferably 0.04% to 0.5% antiseptic, and more preferably still 0.05% to 0.2% antiseptic.

In various embodiments, the second active ingredient comprises:
(a) thiamin, riboflavin, vitamin C, sodium, potassium, glycine, and L-arginine;
(b) thiamin, riboflavin, niacin, Vitamin C, sodium, potassium, glycine and L-arginine;
(c) thiamin, riboflavin, niacin, Vitamin C, pyridoxine, sodium, potassium, glycine, and L-arginine;
(d) thiamin, riboflavin, niacin, Vitamin C, pyridoxine, vitamin B12, sodium, potassium, glycine, and L-arginine;
(e) thiamin, riboflavin, niacin, Vitamin C, pantothenic acid, pyridoxine hydrochloride, vitamin B12, biotin, folate, sodium, potassium, glycine, and L-arginine;
(f) thiamin, riboflavin, niacin, Vitamin C, pantothenic acid, pyridoxine hydrochloride, vitamin B12, biotin, folate, chromium, copper, iodine, magnesium, manganese, molybdenum, selenium, glycine, L-glutamine, L-lysine, L-arginine;
(g) thiamin, riboflavin, vitamin C, sodium, potassium, chloride, glycine, and L-arginine;
(h) thiamin, riboflavin, niacin, Vitamin C, sodium, potassium, glycine and L-arginine;
(i) thiamin, riboflavin, niacin, Vitamin C, pyridoxine, sodium, potassium, chloride, glycine, and L-arginine;
(j) thiamin, riboflavin, niacin, Vitamin C, pyridoxine, vitamin B12, sodium, potassium, chloride, glycine, and L-arginine;
(k) thiamin, riboflavin, niacin, Vitamin C, pantothenic acid, pyridoxine hydrochloride, vitamin B12, biotin, folate, sodium, potassium, chloride, glycine, and L-arginine;
(l) thiamin, riboflavin, niacin, Vitamin C, pantothenic acid, pyridoxine hydrochloride, vitamin B12, biotin, folate, chromium, copper, iodine, magnesium, manganese, molybdenum, selenium, glycine, L-glutamine, L-lysine, L-arginine;
(m) thiamin, riboflavin, vitamin C, sodium, potassium, chlorine, magnesium, glycine, and L-arginine;
(n) thiamin, riboflavin, niacin, Vitamin C, sodium, potassium, chlorine, magnesium, glycine and L-arginine;
(o) thiamin, riboflavin, niacin, Vitamin C, pyridoxine, sodium, potassium, chlorine, magnesium, glycine, and L-arginine;
(p) thiamin, riboflavin, niacin, Vitamin C, pyridoxine, vitamin B12, sodium, potassium, chlorine, magnesium, glycine, and L-arginine;
(q) thiamin, riboflavin, niacin, Vitamin C, pantothenic acid, pyridoxine hydrochloride, vitamin B12, biotin, folate, sodium, potassium, chlorine, magnesium, glycine, and L-arginine;
(r) thiamin, riboflavin, vitamin C, sodium, potassium, chlorine, magnesium, manganese, glycine, and L-arginine;
(s) thiamin, riboflavin, niacin, Vitamin C, sodium, potassium, chlorine, magnesium, manganese, glycine and L-arginine;
(t) thiamin, riboflavin, niacin, Vitamin C, pyridoxine, sodium, potassium, chlorine, magnesium, manganese, glycine, and L-arginine;
(u) thiamin, riboflavin, niacin, Vitamin C, pyridoxine, vitamin B12, sodium, potassium, chlorine, magnesium, manganese, glycine, and L-arginine;
(v) thiamin, riboflavin, niacin, Vitamin C, pantothenic acid, pyridoxine hydrochloride, vitamin B12, biotin, folate, sodium, potassium, chlorine, magnesium, manganese, glycine, and L-arginine;
(w) thiamin, riboflavin, niacin, Vitamin C, pantothenic acid, pyridoxine hydrochloride, vitamin B12, biotin, folate, chromium, copper, iodine, magnesium, manganese, molybdenum, selenium, glycine, L-glutamine, L-lysine, L-arginine;
(x) thiamin, riboflavin, niacin, Vitamin C, pantothenic acid, pyridoxine hydrochloride, vitamin B12, biotin, folate, chromium, copper, iodine, magnesium, manganese, molybdenum, selenium, glycine, L-glutamine, L-lysine, L-arginine;
(y) thiamin, riboflavin, niacin, Vitamin C, pantothenic acid, pyridoxine hydrochloride, vitamin B12, biotin, folate, chromium, copper, iodine, magnesium, manganese, molybdenum, selenium, dextrose, fructose, inulin, glycine, L-glutamine, sodium chloride, potassium chloride, sodium bicarbonate, L-lysine, L-arginine, L-carnitine, Taurine;

In various embodiments, the composition comprises a first active ingredient comprising bis-guanidine compound and a second active ingredient as referred to in (a) to (y) above. Typically, the bis-guanidine compound is chlorhexidine of a chlorhexidine salt. More typically, the bis-guanidine compound is chlorhexidine-digluconate.

In various embodiments, the composition comprises a first active ingredient comprising iodine and a second active ingredient as referred to in (a) to (y) above.

In various embodiments, the composition comprises a first active ingredient comprising an antibacterial dye and a second active ingredient as referred to in (a) to (y) above.

In various embodiments, the composition comprises a first active ingredient comprising a halogenated phenol and a second active ingredient as referred to in (a) to (y) above.

In various embodiments, the composition comprises a first active ingredient comprising a quinolone derivative and a second active ingredient as referred to in (a) to (y) above.

In one embodiment, the glycine and L-arginine in the second active ingredient are in a ratio of glycine:L-arginine in the range from 50:1, 40:1, 30:1, 20:1, 19:1, 18:1, 17:1, 16:1, 15:1.

In an embodiment, sodium is present in an amount of 30 mg to 65 mg per 3.5 g serve, preferably 45 mg to 65 mg.

Sodium is advantageously present in the form of sodium chloride and/or sodium bicarbonate but may be present as any pharmaceutically acceptable salt.

In an embodiment, potassium is present in an amount of 25 mg to 45 mg per 3.5 g serve, preferably 30 mg to 40 mg. Potassium is advantageously present in the form of the potassium chloride but may be present as any pharmaceutically acceptable salt.

In an embodiment, chromium is present in an amount of 10 μg to 20 μg per 3.5 g serve, preferably 15 μg to 19 μg. Typically, chromium is advantageously present in the form of chromium picolinate but may be present as any pharmaceutically acceptable salt.

In an embodiment, copper is present in an amount of 0.1 mg to 0.5 mg per 3.5 g serve, preferably about 0.3 mg. Copper is advantageously present in the form of copper gluconate but may be present as any pharmaceutically acceptable salt.

In an embodiment, iodine is present in an amount of 20 mg to 25 ug per 3.5 g serve. Iodine is advantageously present in the form of potassium iodode but may be present as any pharmaceutically acceptable salt.

In an embodiment, magnesium is present in an amount of 50 mg to 80 mg per 3.5 g serve, preferably 55 mg to 65 mg. Magnesium is advantageously present in the form of magnesium citrate but may be present as any pharmaceutically acceptable salt.

In an embodiment, molybdenum is present in an amount of 5 μg to 20 μg per 3.5 g serve, preferably 7.5 μg to 15 μg. Molybdenum is advantageously present in the form of sodium molybdate but may be present as any pharmaceutically acceptable salt.

In an embodiment, selenium is present in an amount of 5 μg to 20 μg per 3.5 g serve, preferably about 10 μg to 12 μg. Selenium is advantageously present in the form of sodium selenite but may be present as any pharmaceutically acceptable salt.

In an embodiment, thiamin is present in an amount of 10 mg to 30 mg per 3.5 g serve, preferably 15 mg to 25 mg, most preferably about 0.2 mg.

In an embodiment, riboflavin is present in an amount of 0.1 mg to 0.3 mg per 3.5 g serve, preferably 0.15 mg to 0.25 mg.

In an embodiment, niacin is present in an amount of 1 mg to 10 mg per 3.5 g serve, preferably 2 mg to 5 mg.

In an embodiment, vitamin C is present in an amount of 1 mg to 100 mg per 3.5 g serve, preferably 5 mg to 15 mg.

In an embodiment, pantothenic acid is present in an amount of 0.1 mg to 2 mg per 3.5 g serve, preferably 0.5 mg to 1 mg.

In an embodiment, pyridoxine hydrochloride is present in an amount of 0.1 mg to 1 mg per 3.5 g serve, preferably 0.2 mg to 0.5 mg.

In an embodiment, vitamin B12 is present in an amount of 0.1 μg to 1 μg per 3.5 g serve, preferably 0.7 μg to 1 μg.

In an embodiment, biotin is present in an amount of 1 μg to 10 mg per 3.5 g serve, preferably about 5 μg.

In an embodiment, folate is present in an amount of 0.01 mg to 0.1 mg per 3.5 g serve, preferably 0.05 mg to 0.07 mg.

In an embodiment, glutamine is present in an amount of 100 mg to 200 mg per 3.5 g serve, preferably 110 mg to 150 mg, more preferably 115 mg to 125 mg.

In an embodiment, lysine is present in an amount of 20 mg to 100 mg per 3.5 g serve, preferably 40 mg to 60 mg.

In an embodiment, arginine is present in an amount of 10 mg to 30 mg per 3.5 g serve, preferably 15 mg to 25 mg.

In another embodiment, the second active ingredient further comprises at least one, preferably fermentable carbohydrate. In some embodiments, the carbohydrate is selected from the group consisting of dextrose, fructose and inulin.

In an embodiment, each at least one carbohydrate is present in an amount of 100 mg to 1,000 mg per 3.5 g serve. In an embodiment, inulin is present in an amount of 400 mg to 600 mg, fructose in an amount of 200 mg to 300 mg and dextrose in an amount of 800 mg to 1,200 mg.

In one embodiment, the second active ingredient further comprises a component selected from the group consisting of carnitine, glucosamine, taurine, sodium citrate, flaxseed or other Omega 3 rich oil and micellular casein.

In an embodiment, the composition further comprises L-carnitine in an amount of 1 mg to 15 mg per 3.5 g serve, preferably 3 mg to 10 mg, most preferably 5 mg to 7 mg.

In an embodiment, the composition further comprises taurine in an amount of 1 mg to 5 mg per 3.5 g serve, preferably 3 mg to 4 mg.

In one embodiment, the composition is formulated by mixing a gel comprising 0.5% chlorhexidine-digluconate and a powder comprising an admixture of vitamins and minerals in a ratio of 5:1, 4:1, 3:1, 2:1, 1:1, 1:2, 1:3, 1:4 or 1:5, preferably 1:1.

Other agents that may be incorporated into the composition include antiseptic agents, including but not limited to anti-fungal agents, anti-bacterial agents, anti-viral agents and anti-parasitic agents, growth factors, angiogenic factors, anaesthetics, mucopolysaccharides, metals and other healing agents.

Examples of anti-microbial agents that can be used in the present invention include, but are not limited to, isoniazid, ethambutol, pyrazinamnide, streptomycin, clofazimine, rifabutin, fluoroquino tones, ofloxacin, sparfloxacin, rifampin, azithromycin, clarithromycin, dapsone, tetracycline, erythromycin, ciprofloxacin, doxycycline, ampicillin, amphotericin B, ketoconazole, fluconazole, pyrimethamine, sulfadiazine, clindamycin, lincomycin, pentamidine, atovaquone, paromomycin, diclazaril, acyclovir, trifluorouridine, foscarnet, penicillin, gentamicin, ganciclovir, iatroconazole, miconazole, Zn-pyrithione, heavy metals including, but not limited to, gold, platinum, silver, zinc and copper, and their combined forms including, salts, such as chloride, bromide, iodide and periodate, and complexes with carriers, and other forms.

Further agents that may be incorporated into the composition are acid mucopolysaccharides including, but not limited to, heparin, heparin sulfate, heparinoids, dermatan sulfate, pentosan polysulfate, cellulose, agarose, chitin, dextran, carrageenin, linoleic acid, and allantoin; and omega 3-rich oils, such as flaxseed oil.

The compositions of the present disclosure can also be used in combination therapies with opioids and other analgesics, including narcotic analgesics, Mu receptor antagonists, Kappa receptor antagonists, non-narcotic (i.e., non-addictive) analgesics, monoamine uptake inhibitors, adenosine regulating agents, cannabinoid derivatives, Substance P antagonists, neurokinin-1 receptor antagonists and sodium channel blockers, among others. Preferred combination therapies comprise a composition useful in methods described herein with one or more compounds selected from aceclofenac, acemetacin, α-acetamidocaproic acid, acetaminophen, acetaminosalol, acetanilide, acetylsalicylic acid (aspirin), S-adenosylmethionine, alclofenac, alfentanil, allylprodine, alminoprofen, aloxiprin, alphaprodine, aluminum bis (acetylsalicylate), amfenac, aminochlorthenoxazin, 3-amino-4-hydroxybutyric acid, 2-atnino-4-picoline, aminopropylon, aminopyrine, amixetrine, ammonium salicylate, ampiroxicam, amtolmetin guacil, anileridine, antipyrine, antipyrine salicylate, antrafenine, apazone, bendazac, benorylate, benoxaprofen, benzpiperylon, benzydamine, benzylmorphine, bermoprofen, bezitramide, α-bisabolol, bromfenac, p-bromoacetanilide, 5-bromosalicylic acid acetate, bromosaligenin, bucetin, bucloxic acid, bucolome, bufexamac, bumadizon, buprenorphine, butacetin, butibufen, butophanol, calcium acetylsalicylate, carbamazepine, carbiphene, carprofen, carsalam, chlorobutanol, chlorthenoxazin, choline salicylate, cinchophen, cinmetacin, ciramadol, clidanac, clometacin, clonitazene, clonixin, clopirac, clove, codeine, codeine methyl bromide, codeine phosphate, codeine sulfate, cropropamide, crotethamide, desomorphine, dexoxadrol, dextromoramide, dezocine, diampromide, diclofenac sodium, difenamizole, difenpiramide, diflunisal, dihydrocodeine, dihydrocodeinone enol acetate, dihydromorphine, dihydroxyalutninum acetylsalicylate, dimenoxadol, dimepheptanol, dimethylthiambutene, dioxaphetyl butyrate, dipipanone, diprocetyl, dipyrone, ditazol, droxicam, emorfazone, enfenamic acid, epirizole, eptazocine, etersalate, ethenzamide, ethoheptazine, ethoxazene, ethylmethylthiambutene, ethylmorphine, etodolac, etofenamate, etonitazene, eugenol, felbinac, fenbufen, fenclozic acid, fendosal, fenoprofen, fentanyl, fentiazac, fepradinol, feprazone, floctafenine, flufenamic acid, flunoxaprofen, fluoresone, flupirtine, fluproquazone, flurbiprofen, fosfosal, gentisic acid, glafenine, glucametacin, glycol salicylate, guaiazulene, hydrocodone, hydromorphone, hydroxypethidine, ibufenac, ibuprofen, ibuproxam, imidazole salicylate, indomethacin, indoprofen, isofezolac, isoladol, isomethadone, isonixin, isoxepac, isoxicam, ketobemidone, ketoprofen, ketorolac, p-lactophenetide, lefetamine, levorphanol, lofentanil, lonazolac, lomoxicam, loxoprofen, lysine acetylsalicylate, magnesium acetylsalicylate, meclofenamic acid, mefenamic acid, meperidine, meptazinol, mesalamine, metazocine, methadone hydrochloride, methotrimeprazine, metiazinic acid, metofoline, metopon, mofebutazone, mofezolac, morazone, morphine, morphine hydrochloride, morphine sulfate, morpholine salicylate, myrophine, nabumetone, nalbuphine, 1-naphthyl salicylate, naproxen, narceine, nefopam, nicomorphine, nifenazone, niflumic acid, nimesulide, 5'-nitro-2'-propoxyacetanilide, norlevorphanol, normethadone, normorphine, norpipanone, olsalazine, opium, oxaceprol, oxametacine, oxaprozin, oxycodone, oxymorphone, oxyphenbutazone, papaveretum, paranyline, parsalmide, pentazocine, perisoxal, phenacetin, phenadoxone, phenazocine, phenazopyridine hydrochloride, phenocoll, phenoperidine, phenopyrazone, phenyl acetylsalicylate, phenylbutazone, phenyl salicylate, phenyramidol, piketoprofen, piminodine, pipebuzone, piperylone, piprofen, pirazolac, piritramide, piroxicam, pranoprofen, proglumetacin, proheptazine, promedol, propacetamol, propiram, propoxyphene, propyphenazone, proquazone, protizinic acid, ramifenazone, remifentanil, rimazolium metilsulfate, salacetamide, salicin, salicylamide, salicylamide o-acetic acid, salicylsulfuric acid, salsalte, salverine, simetride, sodium salicylate, sufentanil, sulfasalazine, sulindac, superoxide dismutase, suprofen, suxibuzone, talniflumate, tenidap, tenoxicam, terofenamate, tetrandrine, thiazolinobutazone, tiaprofenic acid, tiaramide, tilidine, tinoridine, tolfenamic acid, tolmetin, tramadol, tropesin, viminol, xenbucin, ximoprofen, zaltoprofen and zomepirac (see The Merck Index, 12th Edition (1996), Therapeutic Category and Biological Activity Index, lists therein headed "Analgesic", "Anti-inflammatory" and "Antipyretic").

Still other suitable formulations for use in the present invention can be found in Remington's Pharmaceutical Sciences, 17th Edition (Mack Publishing Company).

The composition comprising the first active ingredient and the second active ingredient may be supplied as a single pre-prepared composition, or the first active ingredient and second active ingredient may be supplied separately and combined shortly before administration to the wound. For example, the second active ingredient may be supplied separately and combined with an antiseptic formulation immediately prior to application to the wound. Thus, the second active ingredient may provide a base composition to which the first active ingredient can be added. Accordingly, one aspect provides a base composition for combining with a first active ingredient comprising an antiseptic to form a composition for enhancing wound healing and/or reduce pain and inflammation in a subject, the base composition comprising the second active ingredient described herein. As used herein, a "base composition" is an intermediate composition to which at least one additional component is added to make the complete composition.

The invention will now be further described by way of reference only to the following non-limiting examples. It should be understood, however, that the examples following are illustrative only, and should not be taken in any way as a restriction on the generality of the invention described above.

EXAMPLES

Example 1

A composition was made by combining the following components 1 and 2 in a 1:1 ratio:
1. A gel comprising 0.5% chlorhexidine-digluconate (commercial known as "Curasept®").
2. A vitamin and mineral powder containing the following per 3.5 gms:

| | |
|---|---|
| Thiamin | 0.21 mg |
| Riboflavin | 0.24 mg |
| Niacin | 2.7 mg |
| Vitamin C | 10 mg |
| Pantothenic Acid | 0.9 mg |
| Pyridoxine Hydrochloride | 0.3 mg |
| Vitamin B12 | 0.9 µg |
| Biotin | 5 µg |
| Folate | 0.06 mg |
| Chromium | 18.2 µg |
| Copper | 0.3 mg |
| Iodine | 23 µg |
| Magnesium | 60 mg |
| Manganese | 0.3 mg |
| Molybdenum | 10 µg |
| Selenium | 10.6 µg |
| Zinc | 2.0 mg |
| Dextrose | 1040 mg |
| Fructose | 280 mg |
| Inulin | 558 mg |
| Glycine | 350 mg |
| L-Glutamine | 120 mg |
| Sodium Chloride | 80 mg |
| Potassium Chloride | 64 mg |
| Sodium Bicarbonate | 64 mg |
| L-Lysine | 45 mg |
| L-Arginine | 19.2 mg |
| L-Carnitine | 6.1 mg |
| Taurine | 3.5 mg |

The combination of 1 and 2 referred to above formed a gel composition which was tested by applying the gel to a 6 mm punch biopsy wound inflicted on mice as set out below.

Methods

Ten C57BL/6 mice were divided into a treatment group and control group (n=5 for each group). Mice were anaesthetised throughout the procedure via the inhalation of 2.5% isofluorane in oxygen. The dorsal surface of each mouse was shaved and the remaining hair removed using depilatory cream. Four circular excisional skin wounds of 6 mm diameter were made on the shaved surface of each mouse using a punch biopsy tool. All tissues were removed down to the panniculus carnosus. Photographs of each set of wounds were taken for each mouse on the day of wounding (D0), and every day up to an including day eight (D8) in order to track wound closure. Photographs were captured using the Xenogen® in vivo imaging system with consistent settings on each day.

Treatment: Following photo capture, 100 μL of chlorhexidine gel was applied using a 1 mL syringe without needle to each individual wound for all mice in the control group. 100 μL of the gel composition prepared in Example 1 (vitamin and mineral powder dissolved in chlorhexidine gel at a concentration of 1 g/g) was applied in the same method as for the control mice to each individual wound for all mice in the treatment group. This procedure was repeated every day from D2 [24 hours post wounding] up to and including D8 [192 hours post wounding], and mice were sacrificed upon completion.

Histological Analysis

Following sacrifice at D8 [192 hours], two wounds from each group were randomly selected and dissected. Wounds were fixed in 4% paraformaldehyde for two hours at four degrees Celsius. Wounds were processed for paraffin histology and embedded in paraffin. 5 μm transverse sections of embedded wounds were prepared onto slides. Slides from each wound were stained using a standard Masson's Trichrome staining procedure, in order to observe and measure collagen deposition in the wound.

Wound Closure

Photographs of each mouse at each time point (D1 to D8) were analysed using the ImageJ software package. Wound closure was measured by calculating the change in number of pixels for each individual wound at each time point, as observed in each captured image. The average rate of wound closure was graphed, and the control and treatment groups were compared against each other.

Results

Wound closure over time is depicted in FIG. 1. Noting that treatment commenced on D2 [48 hours post wounding] for the treatment group, the data clearly indicates that the treatment group has a clear advantage over the control group. A significant difference could be observed in favour of the treatment group on days 7 and 8 (p=0.04 and p=0.03 respectively). The treatment group was 90% healed +/−3% at Day 8 with the control group 77% healed +/−6% at Day8; note there was no overlap of either group's results.

Figure 2:
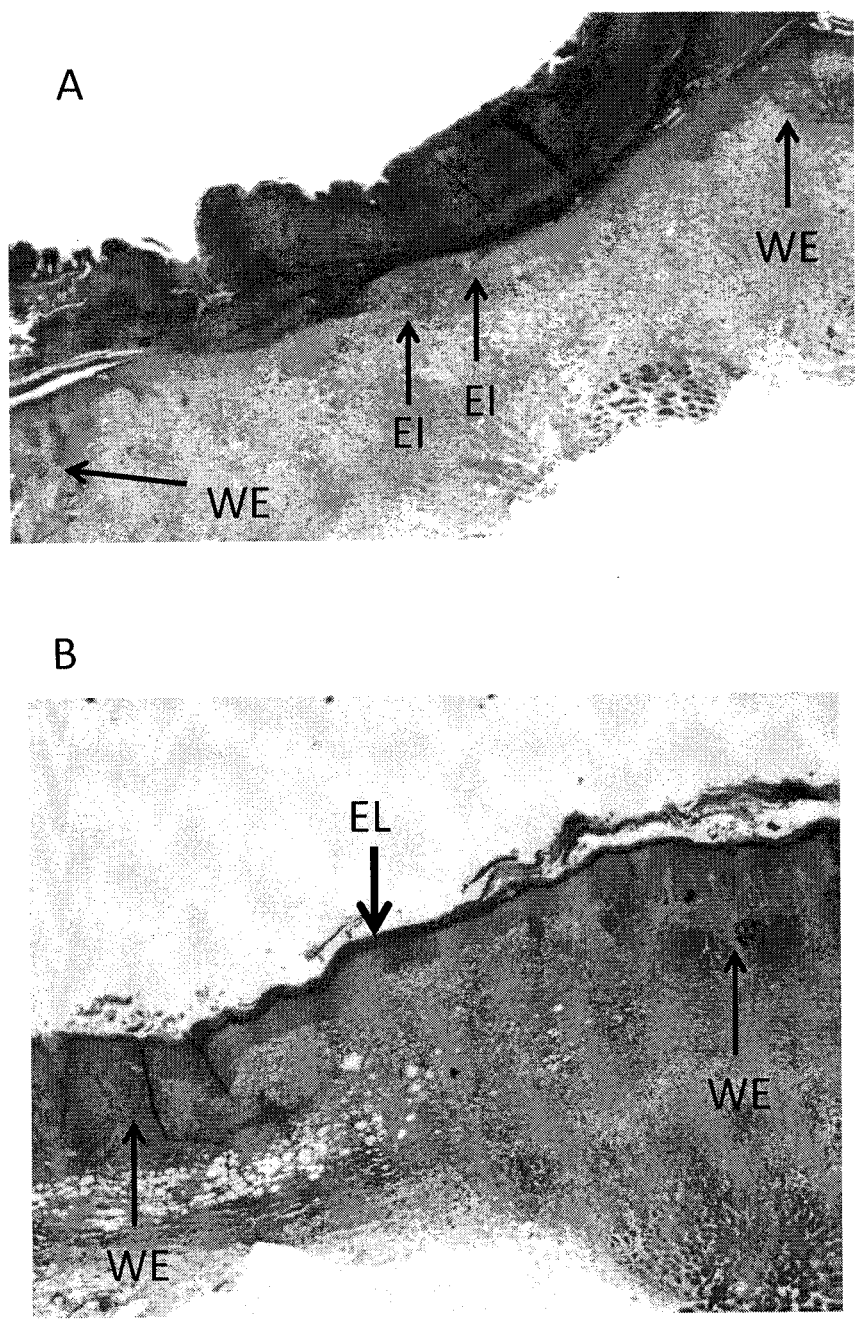
FIG. 2 is a histological section through partially healed wounds from mice selected randomly from a group treated in accordance with the invention (A), and a group treated with antiseptic (B).

The results of Masson's Trichrome blue staining in tissue samples at D8 (192 hours) is shown in FIG. 2. A stained tissue sample from mice treated with the composition prepared in Example 1 is depicted as B in FIG. 2, compared to a stained tissue sample from control mice depicted as A in FIG. 2. Histology of the control group showed signs of sparse collagen deposition at or near the wound edge (WE) by Day 8, with incomplete epithithelisation and residual exudate coverage. The edge of epithelial growth is indicated by EI in FIG. 2A. In contrast to the control, full and early maturing of the epithelial coverage is evident in the treatment group at day 8. In this regard, histology of the treatment group showed diffuse, blue staining collagen deposition speading across the wound edge (the wound edge is labelled WE in FIG. 2B) with skin appendage ingrowth at D8, with complete maturing of the epithelial layer (labelled EL in FIG. 2B).

Example 2

A patient presented to a dental surgery five days after an extraction, with the site of the extraction still open and bleeding and after five days of substantial pain. The pain was severe, rated 8 on a 1 to 10 scale. The patient had been taking Panadeine Forte for that period to obtain pain relief. Relief from pain was almost immediate upon application of the gel composition prepared in Example 1. The patient found that she had to reapply the formulation every 60 to 90 minutes on the day she presented, but woke up the next day with no pain. Redness and inflammation was greatly reduced the following morning. She applied the composition of the invention in the morning and the evening of day 2 and continued to be pain free.

Example 3

A patient presented with painful apthous ulcers on the tongue as well as in the 38 retro-molar region. The pain was rated 10 on a scale of 1 to 10. Following administration of the gel composition prepared in Example 1, the patient reported a reduction in pain from a maximal pain of 10, to 1 (on a scale of 1 to 10) within 20 minutes, and remained relatively pain free; the ulcers were reported to have healed within 48 hours.

Example 4

A 77 year old patient with Type 1 diabetes presented with an incipient gangrene of the large toe. Great concern was held for the vitality of the patients toe and forefoot as circulation has effectively ceased locally.

Figure 3:
FIG. 3 is a photograph of a toe with incipient gangrene following a 2 days of treatment with the composition described herein in combination with penicillin/clavulanic acid (A), 4 days following treatment with the composition described herein (B), 7 days after treatment with the composition (C), and 12 days after treatment with the composition described herein (D).
Figure 3:
Figure 3:
Figure 3:
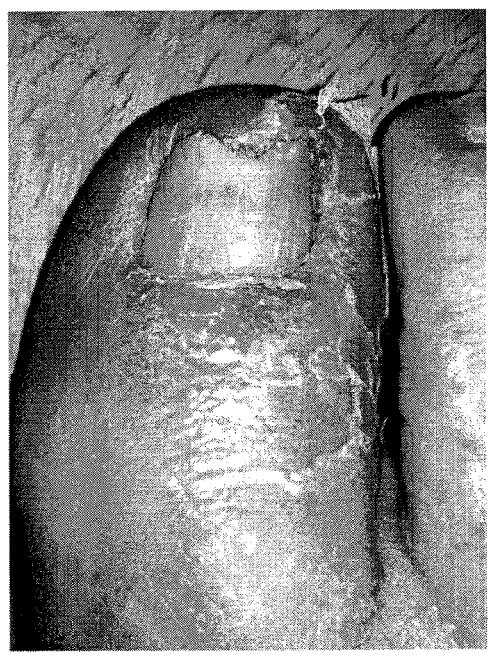

The composition described in Example 1 was applied topically to the toe twice daily initially and then once daily from day 7. FIG. 3A shows the toe following Day 2 of treatment of the toe with the composition described herein combined with a course of penicillin/clavulinic acid for 5 days. FIG. 3B shows the toe at day 4 following treatment with the composition described herein. FIG. 3C shows the toe at day 7 following treatment with the composition described herein. FIG. 3D shows the toe at day 12 following treatment with the composition described herein.

As can be seen from FIG. 3D, there was a marked improvement in the toe by day 12 of treatment with the composition described herein.

Following treatment with the composition described herein, the patient has remained free from further podiatry difficulties.

The invention claimed is:

1. A method for enhancing wound healing and/or reducing pain and inflammation in a subject, said method comprising the steps of administering to a wound of the subject a therapeutically effective amount of a composition comprising a first active ingredient and a second active ingredient, wherein the first active ingredient comprises an antiseptic and the second active ingredient comprises an admixture of carbohydrates, amino acids, at least one vitamin and at least one mineral, wherein the carbohydrates comprise dextrose, fructose and inulin, the amino acids comprise glycine, arginine, glutamine and lysine, wherein the glycine is present in the composition in an amount that is greater than the amount of arginine in the composition.

2. The method of claim 1, wherein said administration is topical administration.

3. The method of claim 1, wherein the dextrose is present in an amount of from 800 mg to 1200 mg per 7 grams of the composition, the fructose is present in an amount of from 200 mg to 300 mg per 7 grams of the composition, and the inulin is present in an amount of from 400 to 600 mg per 7 grams of the composition.

4. The method of claim 1, wherein the glutamine is present in an amount of from 100 mg to 200 mg per 7 grams of the composition, the lysine is present in an amount of from 20 mg to 100 mg per 7 grams of the composition, the arginine is present in an amount of from 10 mg to 30 mg per 7 grams of the composition, and the glycine is present in an amount to give a ratio of glycine to arginine in the range of from 19:1 to 18:1 by weight.

5. The method according to claim 1, wherein said antiseptic is a bis-biguanide compound.

6. The method according to claim 5, wherein said bis-biguanide compound is chlorhexidine or a chlorhexidine salt.

7. The method according to claim 6, wherein the chlorhexidine is chlorhexidine-digluconate.

8. The method according to claim 1, wherein the first active ingredient comprises a bis-biguanide compound at a concentration of 0.01% to 3% by weight.

9. The method according to claim 1, wherein said antiseptic is iodine.

10. The method according to claim 1, wherein said antiseptic is an antibacterial dye.

11. The method according to claim 1, wherein said antiseptic is a halogenated phenol.

12. The method according claim 1, wherein said antiseptic is a quinolone.

13. The method according to claim 1, wherein the mineral is selected from the group consisting of sodium, magnesium, potassium, calcium, zinc, manganese, copper, molybdenum, selenium and chromium or combination thereof.

14. The method according to claim 1, wherein the vitamin is selected from the group consisting of thiamine, riboflavin, niacin, vitamin C, vitamin D, vitamin E, vitamin B, vitamin B12, pantothenic acid, biotin and folate or combination thereof.

15. The method according to claim 1, wherein the second active ingredient further comprises a component selected from, the group consisting of carnitine, glucosamine, taurine, sodium citrate, flaxseed oil and micellular casein or combination thereof.

16. The method according to claim 1, wherein the second active ingredient consists essentially of sodium chloride, magnesium gluconate, potassium chloride, selenium, zinc, sulphate, manganese sulphate, copper sulphate, chromium picolinate, sodium molybdate, potassium iodide, calcium lactate, sodium bicarbonate, L-glycine, L-glutamine, L-lysine, L-arginine, L-carnitine, vitamin C, vitamin D, vitamin B12, niacin, panthothenic acid, riboflavin, pyridoxine, thiamine, folate, biotin, taurine, dextrose, inulin, fructose, dextrose and glycine.

17. The method according to claim 1, wherein the first active ingredient and the second active ingredient are present at a ratio of 5:1, 4:1, 3:1, 2:1, 1:1, 1:2, 1:3, 1:4 or 1:5.

18. The method of claim 1, wherein the wound is the result of infection or inflammation.

19. The method of claim 1, wherein the wound is selected from the group consisting of surgical wound, traumatic mouth ulcer, non-healing area of the mouth, inflammatory lesion and apthous ulcer.

20. The method of claim 17, wherein the first active ingredient and the second active ingredient are present at a ratio of 1:1.

* * * * *